(12) United States Patent
Narimatsu et al.

(10) Patent No.: US 8,623,625 B2
(45) Date of Patent: Jan. 7, 2014

(54) SULFOTRANSFERASE, PEPTIDE THEREOF AND DNA ENCODING THE SAME

(75) Inventors: Hisashi Narimatsu, Tsukuba (JP); Shigemi Sugioka, Tsukuba (JP); Hideo Mochizuki, Nagoya (JP)

(73) Assignee: Seikagaku Corporation, Tokyo (JP)

( * ) Notice: Subject to any disclaimer, the term of this patent is extended or adjusted under 35 U.S.C. 154(b) by 1321 days.

(21) Appl. No.: 11/748,403

(22) Filed: May 14, 2007

(65) Prior Publication Data

US 2008/0187959 A1    Aug. 7, 2008

Related U.S. Application Data

(62) Division of application No. 10/506,548, filed as application No. PCT/JP03/02500 on Mar. 4, 2003, now Pat. No. 7,232,675.

(30) Foreign Application Priority Data

Mar. 4, 2002 (JP) ................ P2002-057527
Aug. 26, 2002 (JP) ................ P2002-245994

(51) Int. Cl.
  *C12N 9/10*      (2006.01)
  *C12N 15/00*     (2006.01)
  *C12N 1/20*      (2006.01)
  *C12P 21/06*     (2006.01)
  *C12P 19/28*     (2006.01)
  *C07H 21/04*     (2006.01)

(52) U.S. Cl.
  USPC ......... 435/193; 435/69.1; 435/85; 435/252.3; 435/320.1; 536/23.2

(58) Field of Classification Search
  None
  See application file for complete search history.

(56) References Cited

U.S. PATENT DOCUMENTS

2002/0086381 A1*  7/2002  Guegler et al. ............... 435/183

FOREIGN PATENT DOCUMENTS

| CN | 1311305 A | 9/2001 |
| WO | 01-90334 A2 | 11/2001 |
| WO | 02-42437 A2 | 5/2002 |

OTHER PUBLICATIONS

Xia G. et al., "Heparan sulfate 3-0-sulfotransferase isoform 5 generates both an antithrombin-binding site and entry receptor for herpes simplex virus, type 1.", J. Biol. Chem., (Oct. 2002), vol. 277, No. 40, pp. 37912-37919.

Shworak NW et al., Molecular cloning and expression of mouse and human cDNAs encoding heparin sulfate D-glucosaminyl 3-O sulfotransferase, J. Biol. Chem., (1997), vol. 272, No. 44, pp. 28008-28019.

* cited by examiner

*Primary Examiner* — Iqbal H Chowdhury
(74) *Attorney, Agent, or Firm* — Sughrue Mion, PLLC

(57) ABSTRACT

A glycosaminoglycan sulfotransferase, a peptide thereof, a nucleic acid comprising a nucleotide sequence encoding the same, an enzyme agent for the synthesis of a glycosaminoglycan, which comprises the above-described enzyme or polypeptide, and a process for producing a glycosaminoglycan, which uses the enzyme agent.

7 Claims, 7 Drawing Sheets

SULFOTRANSFERASE, PEPTIDE THEREOF AND DNA ENCODING THE SAME

This is a divisional of application Ser. No. 10/506,548 filed Sep. 3, 2004, now U.S. Pat. No. 7,232,675 which is a National Stage application of PCT Application No. PCT/JP03/02500, filed Mar. 4, 2003, which claims priority of Japanese Application Nos. JP 2002-057527, filed Mar. 4, 2002, and JP 2002-245994, filed Aug. 26, 2002, the disclosure of each of which is incorporated herein by reference in its entirety.

TECHNICAL FIELD

The present invention relates to a glycosaminoglycan sulfotransferase, a peptide thereof, a nucleic acid comprising a nucleotide sequence encoding the same, an enzyme agent for the synthesis of a glycosaminoglycan, which comprises the above-described enzyme or polypeptide, and a process for producing a glycosaminoglycan, which uses the enzyme agent.

BACKGROUND OF THE INVENTION

Unless otherwise indicated, all of the saccharides and saccharide residues in this description are the D-form optical isomer, excluding iduronic acid. Also, D-glucosamine (which sometimes includes an N-substituted compound) is sometimes referred to as "GlcN", and N-acetyl-D-glucosamine is sometimes referred to as "GlcNAc", D-glucuronic acid is sometimes referred to as "GlcA", L-iduronic acid is sometimes referred to as "IdoA", and hexuronic acid representing a uronic acid having 6 carbon atoms, including GlcA and IdoA, is sometimes referred to as "HexA".

Heparin and heparan sulfate are kinds of glycosaminoglycan having a repeating structure of a disaccharide (4GlcAβ1/IdoAα1→4GlcNAcα1) of HexA residue (GlcA residue or IdoA residue) and GlcNAc residue as the basal skeleton (this basal skeleton may be also referred to as "heparin skeleton" hereinafter), wherein one or more of the 2-position hydroxyl group of its HexA residue and the 2-position amino group, the 3-position hydroxyl group and the 6-position hydroxyl group of its GlcN residue are sulfated.

It has been known so far that the sulfated group of "heparin" or "heparan sulfate" is bound to one or more of the positions shown by $R_1$, $R_2$, $R_3$ and $R_4$ in the following formula (2). However, it has not been known about a glycosaminoglycan in which all of the $R_1$, $R_2$, $R_3$ and $R_4$ are the sulfate group ($SO_3^-$) and a production method thereof.

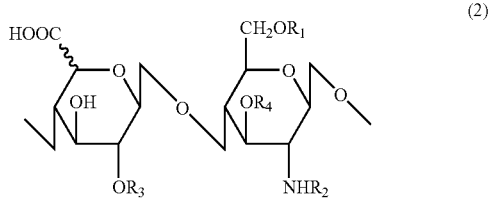

(2)

On the other hand it is generally known that a glycosaminoglycan having the heparin skeleton has various physiological activities. For example, it is known for a long time that heparin shows anticoagulation activity upon blood (*Thronb. Res.*, 75, 1-32 (1994)), and it is known also that it has affinity for various growth factors and carries out a role in stabilizing or activating these growth factors (*Glycobiology*, 4, 451 (1994)). It is known that heparan sulfate also has affinity for various growth factors and accelerates wound healing by stabilizing or activating these growth factors (*J. Phthol*, 183, 251-252 (1997)). In addition, it is known that a 6-O-desulfated heparin which can be obtained by specifically desulfating only the sulfate group bound to the 6-position of GlcN as a constituting saccharide of heparin is deprived of the anticoagulation activity upon blood but has an action to accelerate wound healing (International Publication WO00/06608), and it is known that a periodic acid oxidation-reduction 2-O-desulfated heparin (mainly keeps the heparin skeleton) which can be obtained by a combination of a periodic acid oxidation-reduction treatment and specific desulfation of the 2-position HexA takes a role in stabilizing various growth factors and accelerating nerve growth (JP-A-11-310602).

Based on these facts, it is considered that the glycosaminoglycan having a heparin skeleton has various physiological activities, and it is considered that derivatives of heparin have markedly large possibilities.

On the other hand, since the gene encoding a glycosaminoglycan sulfotransferase has been cloned, it is considered that information on the substrate specificity of the enzyme for glycosaminoglycan as the sulfate group acceptor can be obtained by preparing the enzyme in a large amount, which will provide a useful approach in studying relationship between the structure and the function of glycosaminoglycan. It is known that there are many sulfation processes in the synthesis of glycosaminoglycan, particularly in the synthesis of heparin/heparan sulfate (*Glycotechnology*, (5), 57 (1994), published by Kodansha Scientific), and it is considered that various types of glycosaminoglycan sulfotransferases are concerned in this sulfation. Regarding the glycosaminoglycan sulfotransferase which transfers a sulfate group to heparin/heparan sulfate, heparan sulfate N-deacetyl/N-sulfotransferase (hereinafter sometimes referred to as "NDST"), heparan sulfate 2-O-sulfotransferase (hereinafter sometimes referred to as "HS2ST"), heparan sulfate 3-O-sulfotransferase (hereinafter sometimes referred to as "HS3OST"), heparan sulfate 6-O-sulfotransferase (hereinafter sometimes referred to as "HS6ST") and the like have been isolated from various organisms, particularly from human, and their cDNA molecules have been cloned.

A cDNA of human HS3OST has been disclosed in *J. Biol. Chem.*, 272, 28008-28019 (1997), and the cDNA described in the reference has been registered at GenBank as accession number AF019386.

Although an enzyme which can transfer a sulfate group to a glycosaminoglycan having a heparin skeleton is markedly useful because of its high possibility to be used in the enzymatic synthesis of heparin and heparan sulfate, such an enzyme has high substrate specificity so that it is necessary to carry out the synthesis efficiently by using various types of the enzyme for the purpose of industrially synthesizing various types of heparin and heparan sulfate. However, it cannot be said yet that there are sufficient variations of the enzyme capable of transferring a sulfate group to the heparin skeleton.

Accordingly, in the case where production of a glycosaminoglycan having a new structure becomes possible by using an enzyme, it becomes possible to search for a physiological activity possessed by such a glycosaminoglycan.

DISCLOSURE OF THE INVENTION

An object of the invention is to provide a novel sulfotransferase and also provide a means for obtaining the enzyme in a large amount by a convenient method through cloning of a cDNA encoding the amino acid sequence of the polypeptide to thereby increase variations of glycosaminoglycan which can be synthesized by enzyme chemistry and also contribute to the elucidation of structure-function relationship of glycosaminoglycan having heparin skeleton.

Accordingly, the invention relates to the followings.

(1) A polypeptide which comprises amino acid numbers 37 to 346 in the amino acid sequence represented by SEQ ID NO:2, or a polypeptide of a sulfotransferase which comprises an amino acid sequence having substitution, deletion, insertion, addition and/or transposition of at least one amino acid in the amino acid sequence and has activity of transferring a sulfate group from a sulfate group donor to a glycosaminoglycan which is a sulfate group acceptor.

(2) The polypeptide according to (1), which consists of the amino acid sequence represented by SEQ ID NO:2.

(3) The polypeptide according to (1), which consists of amino acid numbers 37 to 346 in the amino acid sequence represented by SEQ ID NO:2.

(4) The polypeptide according to any one of (1) to (3), wherein the glycosaminoglycan is heparin or heparan sulfate.

(5) A sulfotransferase which comprises the polypeptide according to any one of (1) to (4) and has activity of transferring a sulfate group from a sulfate group donor to a glycosaminoglycan which is a sulfate group acceptor.

(6) A nucleic acid which encodes the polypeptide according to any one of (1) to (4) or the sulfotransferase according to (5).

(7) A nucleic acid which consists of the nucleotide sequence represented by SEQ ID NO:1.

(8) A nucleic acid which hybridizes with the nucleic acid according to (6) or (7) or a nucleic acid consisting of a nucleotide sequence complementary to the nucleotide sequence under stringent conditions.

(9) An expression vector which comprises the nucleic acid according to any one of (6) to (8).

(10) A recombinant which comprises the expression vector according to (9).

(11) A recombinant which comprises a host cell into which the expression vector according to (9) is introduced.

(12) A process for producing a polypeptide or a sulfotransferase, which comprises growing the recombinant according to (10) or (11), and recovering the polypeptide according to any one of (1) to (4) or the sulfotransferase according to (5) from the obtained grown recombinant.

(13) An enzyme agent for synthesizing a glycosaminoglycan comprising the structure represented by the following formula (1), which comprises the polypeptide according to any one of claims 1 to 4 or the sulfotransferase according to claim 5:

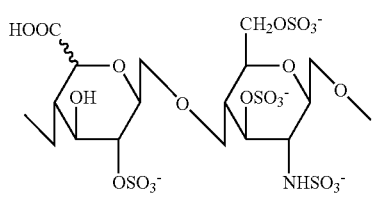

(14) A process for producing a glycosaminoglycan comprising the structure represented by the following formula (1), which comprises reacting the enzyme agent according to (13) with heparin or heparan sulfate to transfer a sulfate group from a sulfate group donor to a sulfate group acceptor:

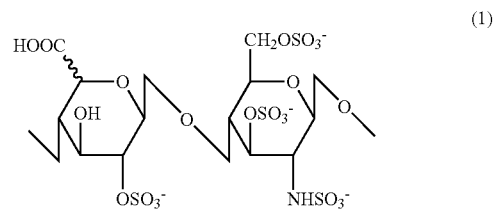

(15) Use of the polypeptide according to any one of (1) to (4) or the sulfotransferase according to (5) as a catalyst for synthesizing a glycosaminoglycan comprising the structure represented by the following formula (1).

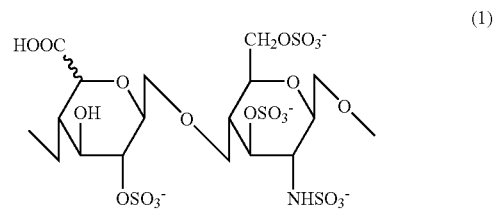

BEST MODE FOR CARRYING OUT THE INVENTION

Figure 1:
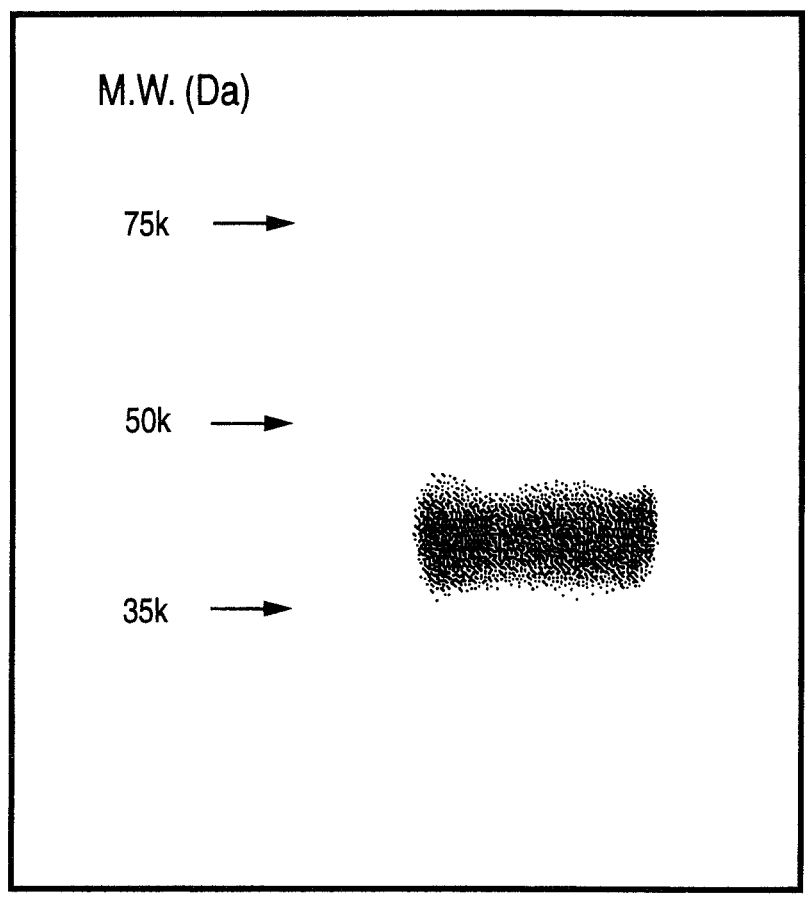
FIG. 1 is a photograph showing Western blotting analysis of purified SFT-1-FLAG described in Examples.

The present inventors have conducted intensive search on a DNA comprising a nucleotide sequence encoding glycosaminoglycan sulfotransferase capable of sulfating heparan sulfate and found a novel DNA having a nucleotide sequence encoding a polypeptide of the enzyme, and have confirmed that the glycosaminoglycan sulfotransferase can be obtained by expressing the DNA and that glycosaminoglycan having a new structure can be produced by using the glycosaminoglycan sulfotransferase. Thus, the invention has been accomplished.

The embodiments of the invention are described below.

(1) Enzyme of the Invention/Polypeptide of the Invention

The enzyme of the invention is a glycosaminoglycan sulfotransferase (SFT-1) which comprises a polypeptide comprising an amino acid sequence consisting of at least amino acid numbers 37 to 346 in the amino acid sequence represented by SEQ ID NO:2 and also has activity of transferring a sulfate group from a sulfate group donor to a glycosaminoglycan which is a sulfate group acceptor.

Examples of the polypeptide according to the enzyme of the invention (hereinafter sometimes referred to as "polypeptide of the invention") include a polypeptide consisting of amino acid numbers 1 to 346 represented by SEQ ID NO:2 and a polypeptide consisting of an amino acid sequence consisting of amino acid numbers 37 to 346 in the amino acid sequence represented by SEQ ID NO:2. It is preferred that the polypeptides are derived from a mammal, particularly desirably from human. Among the polypeptides, a polypeptide consisting of an amino acid sequence consisting of amino acid numbers 37 to 346 which excludes the presumed transmembrane region from the amino acid sequence represented by SEQ ID NO:2 (a region consisting of amino acid numbers 1 to 36 in SEQ ID NO:2) is particularly preferred since it becomes a so-called solubilized form which facilitates its preparation and application.

In general, it is known that the enzyme activity is maintained when one or plural (generally from 2 to 34) constituting amino acids in an amino acid sequence of an enzyme protein are substituted, deleted, inserted, added and/or transpositioned, so that it can regarded as a variant of the same enzyme, and in the case where partial mutations such as substitution, deletion, insertion, addition and/or transposition of one or plural (generally from 2 to 34) constituting amino acids are also generated in the amino acid sequence represented by SEQ ID NO:2 of the polypeptide of the invention, this can be regarded as a substance which is substantially identical to the polypeptide of the invention, so long as it keeps the sulfate group transferring activity which is described later (such a polypeptide having partial mutations in the polypeptide comprising the amino acid sequence represented by SEQ ID NO:2 is described as "a modified polypeptide" for the sake of convenience). It is preferred that the amino acid sequence of the modified polypeptide has a homology of 90% or more, preferably 95% or more, more preferably 97% or more, with the amino acid sequence represented by SEQ ID NO:2. The homology of the amino acid sequence can be easily calculated by using conventionally known computer software such as FASTA, and the software can also be provided by internet.

Also, in the above-described polypeptide of the invention, a saccharide chain can be linked to a constituting amino acid of the polypeptide, so long as its amino acid sequence is the same as described above and it has the above-described enzyme activity. That is, an embodiment of glycoprotein is included in the polypeptide of the invention as a matter of course.

The sulfate group donor used in the reaction of the enzyme of the invention is not particularly limited, so long as it is a substance capable of transferring the sulfate group to a glycosaminoglycan which is a sulfate group acceptor, but 3'-phosphoadenosine 5'-phosphosulfate (active sulfate: hereinafter referred also to as "PAPS") which is generally known to function as a sulfate group donor in the living body is preferred due to a high possibility that it is a sulfate group donor for the enzyme of the invention in the living body.

Examples of the glycosaminoglycan as the sulfate group acceptor for the enzyme of the invention include hyaluronic acid, chondroitin, chondroitin sulfate, dermatan sulfate, keratan sulfate, heparan sulfate, heparin and the like, glycosaminoglycan having the so-called heparin skeleton such as heparan sulfate or heparin is particularly preferred, and heparan sulfate is most particularly preferred. Also, as is also apparent from the following Examples, the enzyme of the invention does not substantially have activity of transferring a sulfate group to shark cartilage-derived chondroitin sulfate, chondroitin obtained by desulfating bovine bronchus-derived chondroitin sulfate, swine skin derived dermatan sulfate and desulfated dermatan sulfate prepared by removing sulfate group from cockscomb-derived dermatan sulfate.

It is possible to easily confirm the sulfate group transferring activity of the enzyme of the invention, for example, by carrying out the enzyme reaction in a buffer at a temperature of 20 to 40° C. by using PAPS labeled with a label such as a radioisotope ($^{35}$S, $^3$H (tritium) or the like) or a fluorescent material (a radioisotope is preferred since it does not generate steric hindrance in the substrate) and also by using a glycosaminoglycan which is a sulfate group acceptor, and then examining whether or not the acceptor is labeled with the label, for example, by checking the reaction solution after the reaction through the combination of a separation means such as gel filtration or high performance liquid chromatography (hereinafter also referred to as "HPLC") with a label-detecting means (radioactivity detecting means such as a scintillation counter or autoradiography when a radioisotope is used as the label, or detection by a fluorescence detector when a fluorescent material is used as the label).

Since the enzyme of the invention obtained in this manner has activity of specifically transferring the sulfate group to a glycosaminoglycan, particularly to heparin and heparan sulfate, it is possible to use this as the enzyme agent of the invention which is described later.

(2) Nucleic Acid of the Invention, Expression Vector of the Invention and Recombinant of the Invention The nucleic acid of the invention is a nucleic acid which encodes the enzyme of the invention or polypeptide of the invention.

The nucleic acid of the invention is not limited to deoxyribonucleic acid (DNA) or ribonucleic acid (RNA), so long as it encodes the enzyme of the invention or polypeptide of the invention, and it may be either single-stranded or double-stranded. However, since the above-described enzyme of the invention and polypeptide of the invention are human-derived amino acid sequences, it is preferable that it is a DNA capable of encoding a polypeptide in many organisms including human.

The term "nucleic acid encoding" as used herein means both of a nucleic acid consisting of a nucleotide sequence complementary to the nucleotide sequence of a template chain to be used as the template for mRNA synthesis and a nucleic acid consisting of a nucleotide sequence of the template chain, generally in the transcription in protein (polypeptide) synthesis.

Examples of the nucleotide sequence of such a nucleic acid include the nucleotide sequence represented by SEQ ID NO:1, a nucleotide sequence consisting of nucleotide numbers 109 to 1041 (a nucleotide sequence corresponding to the coding region of the amino acid numbers 37 to 346) in the nucleotide sequence represented by SEQ ID NO:1, and nucleotide sequences complementary to these nucleotide sequences, and nucleic acids consisting of such nucleotide sequences are included in the nucleic acid of the invention.

In addition, it is known that a single-stranded nucleic acid hybridizes with a nucleic acid comprising a nucleotide sequence complementary thereto under certain conditions, and the nucleic acid of the invention includes nucleotide chains consisting of the nucleotide sequence represented by SEQ ID NO:1, a nucleotide sequence consisting of nucleotide numbers 109 to 1041 in the nucleotide sequence represented by SEQ ID NO:1, and nucleotide sequences complementary to these nucleotide sequences under stringent conditions.

Examples of the stringent conditions include conditions of 42° C. in the presence of 50% formamide, 5×SSPE (sodium chloride/sodium phosphate/EDTA (ethylenediaminetetraacetic acid) buffer), 5×Denhardt's solution, 0.5% SDS (sodium dodecyl sulfate) and 100 µg/ml of denatured salmon sperm DNA, and under conditions substantially identical thereto. That is, the stringent conditions are conditions employed in the general hybridization of genes and included in the term "under stringent conditions" as used herein, so long as they are conditions used in the screening and the like which use Northern blotting, Southern blotting or hybridization.

The DNA which consists of the nucleotide sequence consisting of nucleotide numbers 109 to 1041 in the nucleotide sequence represented by SEQ ID NO:1, which is one of the preferred illustrative embodiments of the nucleic acid of the invention, can be prepared by the method described in the following Examples, or since the complete nucleotide sequence thereof has been found by the invention, it can also be prepared by carrying out a polymerase chain reaction (hereinafter also referred to as "PCR") in the usual way, for example, by using a human-derived cDNA library as the template and using a 5' primer (SEQ ID NO:3) and 3' primer (SEQ ID NO:4). In the same manner, a DNA consisting of the nucleotide sequence represented by SEQ ID NO:1 can also be prepared by carrying out PCR using a primer represented by SEQ ID NO:5 as the 5' primer and a primer represented by SEQ ID NO:4 as the 3' primer.

The expression vector of the invention contains the above-described nucleic acid of the invention, which is generally constituted by the nucleic acid of the invention as a DNA and a conventionally known basal vector (a plasmid, phage, virus or the like) into which the enzyme of the invention is introduced, and is constructed in such a manner that the enzyme of the invention or polypeptide of the invention can be expressed in a host cell.

The basal vector to be used as the above-described expression vector of the invention can be optionally selected by those skilled in the art according to the host cell used, and the expression vector of the invention can be constructed by ligating the above-described nucleic acid of the invention to the thus selected basal vector in the usual way.

In addition, in order to facilitate its secretion, isolation, purification and analysis in preparing the enzyme of the invention or polypeptide of the invention by expressing the expression vector of the invention, the enzyme of the invention or polypeptide of the invention may be constructed in such a manner that it can be expressed as a fusion protein with a marker peptide. In the arrangement of the enzyme of the invention or polypeptide of the invention and the marker peptide in this case, the marker peptide may be bound to the C-terminal side of the enzyme of the invention or polypeptide of the invention or to the N-terminal side thereof. In addition, such a binding when made via a spacer consisting of an amino acid sequence having no physiological activity (a peptide consisting of about 2 to 10 amino acids) is not limited, so long as the enzyme of the invention or polypeptide of the invention has activity of transferring a sulfate group from a sulfate group donor to a glycosaminoglycan which is the sulfate group acceptor.

The marker peptide means any peptide, for example, selected from the group consisting of a signal peptide (a peptide consisting of 15 to 30 amino acid residues, which is present in the N-terminus of many proteins and functioning intracellularly for the selection of a protein: e.g., OmpA, OmpT, Dsb or the like), protein kinase A, protein A (a protein of about 42,000 in molecular weight, which is a constituting component of *Staphylococcus aureus* cell wall), glutathione S transferase, His tag (a sequence of 6 to 10 histidine residues), myc tag (a sequence of 13 amino acid residues, derived from cMyc protein), FLAG peptide (a marker for analysis consisting of a sequence of 8 amino acid residues), T7 tag (a sequence of the first 11 amino acid residues of gene 10 protein), S tag (a sequence of 15 amino acid residues, derived from pancreatic RNase A), HSV tag, pel B (a sequence of 22 amino acid residues of *Escherichia coli* outer membrane protein pel B), HA tag (a sequence of 10 amino acid residues, derived from hemagglutinin), Trx tag (thioredoxin sequence), CBP tag (a calmodulin binding peptide), CBD tag (a cellulose binding domain), CBR tag (a collagen binding domain), β-lac/blu (β-lactamase), β-gal (β-galactosidase), luc (luciferase), HP-Thio (His-patch thioredoxin), HSP (heat shock protein), Lnγ (laminin γ peptide), Fn (fibronectin partial peptide), GFP (green fluorescent peptide), YFP (yellow fluorescent peptide), CFP (cyan fluorescent peptide), BFP (blue fluorescent peptide), DsRed, DsRed2 (red fluorescent peptide), MBP (maltose binding peptide), LacZ (lactose operator), IgG (immunoglobulin G), avidin and protein G, and any one of these marker peptides can be used. Among these, signal peptide, protein kinase A, protein A, glutathione S transferase, His tag, myc tag, FLAG tag, T7 tag, S tag, HSV tag, pelB and HA tag are particularly preferred since expression of the enzyme of the invention and polypeptide of the invention by genetic engineering techniques and their secretion, isolation, purification and analysis become more easy.

As the host cell into which the expression vector of the invention is to be introduced, it is possible to use either a procaryotic cell (e.g., *Escherichia coli* or the like) or a eucaryotic cell (e.g., yeast, insect cell, mammalian cell or the like). Particularly, in the case where a procaryotic cell is used as the host cell, saccharide chain addition and the like do not occur when the nucleic acid of the invention is expressed, so that the peptide of the invention to which saccharide chains are not added can be obtained. However, since the enzyme of the invention or polypeptide of the invention is an enzyme or polypeptide generally expressed in eucaryote, a eucaryotic cell is preferred as the host cell, and its preferred examples include insect cells (they are superior in terms of the large scale synthesis of the enzyme of the invention or polypeptide of the invention) or mammalian cells (they are superior in terms that they are cells in which the enzyme of the invention is originally expressed).

The recombinant of the invention is a cell in which the vector of the invention constructed using a suitable basal vector into such a host cell in the usual way.

(3) Enzyme Production Method of the Invention

The enzyme production method of the invention is a method for producing the polypeptide of the invention or enzyme of the invention, wherein the recombinant of the invention is allowed to grow, and the polypeptide of the invention or enzyme of the invention is recovered from the thus obtained grown material.

The method for growing the recombinant of the invention can be carried out by those skilled in the art by optionally selecting a method suitable for the host cell used in the recombinant. Also, the term "grow" is a general idea of not only culturing the recombinant in outside of a living body, for example, by using a culturing apparatus or a culturing tool, but also propagating it in the living body by administering the host cell to the living body.

The grown material in the production method of the invention includes a medium obtained by culturing the cell in the outside of the living body and the cultured recombinant itself, as well as excrements, secretions, body fluids, tissues and the like of the living body obtained when the recombinant is grown in the living body.

As the recovery of the polypeptide of the invention from a grown material, it is possible to separate the polypeptide of the invention, for example, by a separation means such as gel filtration or HPLC which is based on the difference in molecular weight and a separation means such as an affinity column in which a sulfate group donor (PAPS or the like) in the enzyme reaction of the polypeptide of the invention is made into a solid phase, or in the case where the polypeptide of the invention is expressed as a fusion protein with a marker peptide, by a means for specifically adsorbing the marker peptide. For example, in the case where FLAG peptide is used as the marker peptide, it is possible to obtain the polypeptide of the invention easily as its fusion protein with the FLAG peptide by using an affinity column in which an anti-FLAG antibody is made into a solid phase.

(4) Enzyme Preparation of the Invention

The enzyme agent of the invention is an "enzyme agent for the synthesis of a glycosaminoglycan which comprises a structure represented by the following formula (1) and comprises the enzyme of the invention or polypeptide of the invention".

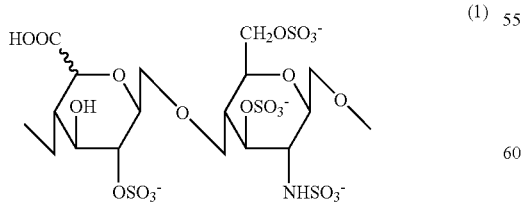

(1)

Also, according to this description, the symbol ∿ in the formula (1) means that the projecting direction of the carboxyl group against the saccharide ring is not limited.

The "polypeptide of the invention" and the "enzyme of the invention" according to the above-described enzyme agent of the invention are "a polypeptide of an enzyme having activity of forming a glycosaminoglycan comprising the structure of above-described formula (1) (sulfotransferase activity), by transferring a sulfate group from a sulfate group donor to a glycosaminoglycan which is a sulfate group acceptor, upon heparin or heparan sulfate" and an enzyme comprising the polypeptide, respectively, which are contained as the active component of the enzyme agent of the invention.

In addition, the "sulfate donor" in the enzyme reaction by the enzyme agent of the invention is not particularly limited, so long as it is "a substance capable of transferring a sulfate group to a glycosaminoglycan which is a sulfate group acceptor", and PAPS which is known to generally function as the sulfate group donor for the enzyme of the invention in the living body.

Also, in addition to the active components, the "enzyme agent of the invention" may further contain a carrier (cellulose gel, agarose gel, silica gel, glass beads or the like), a stabilizer or filler for stabilizing the same or making a pharmaceutical preparation, other polypeptide (e.g., a marker peptide or the like for forming a fusion protein with the "peptide of the invention" in the case where the "polypeptide of the invention" is synthesized by genetic engineering techniques) or a saccharide chain (e.g., a saccharide chain is added to the polypeptide of the invention in some cases when a eucaryote-derived cell is used as the host in synthesizing the "enzyme of the invention" or "polypeptide of the invention" by genetic engineering techniques), without problems, so long as they do not hinder the sulfotransferase activity possessed by the polypeptide of the invention or enzyme of the invention.

Such an enzyme agent of the invention can be used in a method for producing heparin or heparan sulfate comprising the structure of the following formula (1), by transferring sulfate group from a "sulfate group donor" to a glycosaminoglycan (saccharide chain production method of the invention).

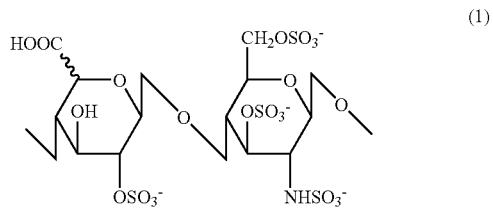

(1)

(5) Sugar Chain Production Method of the Invention

The glycosaminoglycan obtained by the saccharide chain production method of the invention is a "glycosaminoglycan having the heparin skeleton which contains a disaccharide represented by the following formula (1) as the basal skeleton".

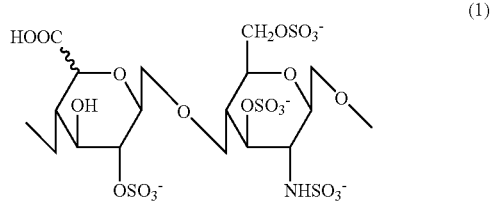

(1)

In addition, the above-described formula (1) is more specifically disaccharides represented by the following formulae (3) and (4), and either one of the disaccharides is contained at a frequency of one or more, preferably 3 or more, and more preferably 5 or more, per molecule of the "product by the saccharide chain production method of the invention".

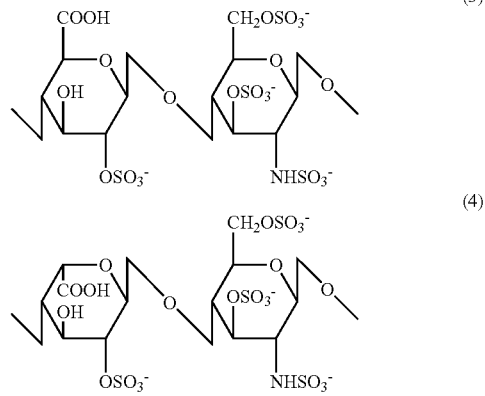

Since the "product by the saccharide chain production method of the invention" is prepared by allowing the above-described "enzyme agent of the invention" to react as the catalyst upon a glycosaminoglycan, its weight average molecular weight is a weight average molecular weight close to that of the heparin or heparan sulfate used as the material. For example, the weight average molecular weight of the "product by the saccharide chain production method of the invention", measured by gel filtration, is from 3,000 to 30,000 Da, preferably from 4,000 to 27,000 Da, and most preferably from 5,000 to 25,000 Da.

The invention is described below more illustratively based on Examples, but the invention is not limited thereto.

Example 1

Search of Gene Data Base and Determination of Nucleotide Sequence of the Nucleic Acid of the Invention Using a conventionally known human-derived heparan sulfate 3-O-sulfotransferase (HS3OST) gene, analogous genes from a gene data base were searched. The sequence used was SEQ ID NO:AFO19836 of the HS3OST gene. In this case, Blast [Altschul et al., *J. Mol. Biol.,* 215, 402-410 (1990)] was used in the search.

As a result, an analogous sequence was found in a genomic sequence GeneBank Accession No. AL 355498, and a novel gene having homology with the HS3OST gene was identified. It was estimated by a gene analyzing program (GENSCAN: manufactured by Stanford University) that this novel gene is encoded by two exons.

(1) Confirmation of Coding Region of the Polypeptide of the Invention

Using Human Kidney Marathon-Ready cDNA (manufactured by CLONTECH), PCR (35 cycles of 94° C. for 5 seconds and 68° C. for 4 minutes) was carried out with the attached AP1 primer (AP1 and AP2 adapters are attached to both ends of a cDNA fragment) and a primer set up to a sequence moiety around the 5'-terminus of the second exon (GP-226: SEQ ID NO:6). Subsequently, nested PCR (40 cycles of 94° C. for 5 seconds and 68° C. for 4 minutes) was carried out with the AP2 primer attached to the Marathon cDNA and a primer set up to the sequence moiety (GP-224: SEQ ID NO:7). The PCR product obtained as the result was subjected to an agarose gel electrophoresis, and a band of about 450 b was recovered by using Gel Extraction Kit (manufactured by QIAGEN). As a result of the analysis of the nucleotide sequence of the thus obtained DNA fragment by a conventional method, a sequence of the second exon was confirmed in succession to a sequence of the first exon (N-terminal 36 amino acids were encoded). The sequence was the same as that predicted by the gene analysis program. Accordingly, it was confirmed that the coding region for the polypeptide of the invention is the sequence shown in SEQ ID NO:1 in which the first exon and the second exon are bound to each other.

(2) Cloning of Second Exon

Based on the above results, those which are encoded by the first exon are only the N-terminal 36 amino acids. Since the second exon encodes the majority of the polypeptide of the invention, it was considered that the principal part of the enzyme including the active region is contained in the second exon (the polypeptide of the invention encoded by the second exon is called SFT-1 for the sake of convenience). Accordingly, cloning of the second exon moiety was carried out by using a genomic DNA as the template.

Using Human Genomic DNA (manufactured by CLONTECH) as the template, PCR (35 cycles of 94° C. for 15 seconds, 50° C. for 30 seconds and 68° C. for 1 minute) of a region containing the second exon was carried out. The primers used were set to the genomic sequences of an upstream moiety of the second exon (SFTex2F: SEQ ID NO:8) and a downstream moiety of the termination codon (SFTex2R: SEQ ID NO:9). The thus obtained fragment of about 1 kb was purified in the usual way, and its nucleotide sequence was analyzed to confirm that the sequence of the second exon was obtained.

Example 2

Introduction of SFT-1 Gene into Expression Vector

In order to prepare a gene expression system, the second exon DNA obtained above was firstly introduced into an expression vector pDONR201 of the Gateway system manufactured by Invitrogen, and Bacmid was further prepared by the Bac-to-Bac system manufactured by Invitrogen. The details are explained below.

(1) Preparation of Entry Clone for the Novel Sulfotransferase

Using the PCR product obtained above by amplifying the second exon as the template, PCT (30 cycles of 94° C. for 15 seconds and 68° C. for 3 minutes) was again carried out to obtain a DNA fragment for used in the Gateway system. The primers used were a 5' primer (SFTgateF2: SEQ ID NO:10) and a 3' primer (SFTgateRstop: SEQ ID NO:11), prepared by adding a sequence for Gateway system to a sequence close to the 5'-terminus of the second exon and a sequence close to the termination codon. The DNA fragment was purified in the usual way and introduced into pDONR201 by a BP clonase reaction to prepare an entry clone. The reaction was carried out by incubating 1 µl of the DNA fragment of interest, 1 µl (150 ng) of pDONR201, 2 µl of a reaction buffer, 4 µl of Tris-ethylenediaminetetraacetic acid (EDTA) buffer (hereinafter sometimes referred to as "TE") and 2 µl of BP clonase mix, at 25° C. for 1 hour. The reaction was terminated by adding 1 µl of proteinase K and keeping at 37° C. for 10 minutes.

Thereafter, 5 µl of the above-described reaction solution was mixed with 100 µl of competent cells (*Escherichia coli* DH5α) to carry out transformation by a heat shock method, and then the cells were spread on the LB medium containing kanamycin. A colony was picked up on the next day and cultured in 3 ml of LB medium containing kanamycin, and then plasmid was extracted and purified using QIAprep Spin Miniprep Kit (manufactured by QIAGEN). Using a part of the thus obtained plasmid, its nucleotide sequence was analyzed by a conventional method to confirm that the DNA of interest has been introduced.

(2) Preparation of Expressing Clone

The above-described entry clone has attL which is a recombination region when λ phage is cut out from *Escherichia coli*, on both sides of its insertion site, and the insertion site is transferred to a destination vector by mixing LR clonase (a mixture of recombinases Int, IHF and Xis) with the destination vector so that a expressing clone is prepared. The specific steps are as follows.

Firstly, 1 µl of the entry clone, 0.5 µl (75 ng) of pFBIF, 2 µl of LR reaction buffer, 4.5 µl of TE and 2 µl of LR clonase mix were allowed to react at 25° C. for 1 hour, and the reaction was terminated by adding 1 µl of proteinase K and incubating at 37° C. for 10 minutes (pFBIF-SFT-1 is purified by this recombination reaction). The pFBIF is prepared by inserting Igκ signal sequence (SEQ ID NO:12) and FLAG peptide (SEQ ID NO:13) into pFastBac1, and in order to insert Gateway sequence by inserting a DNA fragment obtained by primers OT20 (SEQ ID NO:15) and OT21 (SEQ ID NO:16) using OT3 (SEQ ID NO:14) as the primer into the BamHI and EcoRI sites in the same manner as described above, a conversion cassette was inserted using Gateway Vector Conversion System (manufactured by Invitrogen). The Igκ signal sequence was inserted to convert the expressed protein into secretion type, and the FLAG tag to facilitate its formation.

Thereafter, 5 µl of the above-described reaction solution was mixed with 50 µl of competent cells (*Escherichia coli* DH5α), followed by transformation by a heat shock method, and then the cells were spread on the LB medium containing ampicillin. A colony was picked up on the next day and cultured in 5 ml of LB medium containing ampicillin, and then the plasmid (pFBIF-SFT-1) was extracted and purified using QIAprep Spin Miniprep Kit (manufactured by QIAGEN). Using a part of the thus obtained plasmid, its nucleotide sequence was analyzed by a conventional method to confirm that the DNA of interest has been introduced.

(3) Preparation of Bacmid by Bac-to-Bac System

Next, the sequence of SFT-1 was inserted into Bacmid capable of multiplying in insect cells, by carrying out recombination between the above-described pFBIF-SFT-1 and pFastBac using the Bac-to-Bac system (manufactured by Invitrogen). This system is a system in which a gene of interest is incorporated into Bacmid by a recombinant protein produced from a helper plasmid, by simply introducing the gene of interest-inserted pFastBac into a Bacmid-containing *Escherichia coli* strain (*E. coli* DH10BAC) by using the recombination region of Tn7. In addition, since the lacZ gene is contained in Bacmid, it is possible to carry out the classical selection based on the color of colonies (blue (no insertion)-white (insertion)).

That is, the above-described purified vector (pFBIF-SFT-1) was mixed with 50 µl of competent cells (*Escherichia coli* DH10BAC), followed by transformation by a heat shock method, the resulting cells were spread on the LB medium containing kanamycin, gentamicin, tetracycline, 5-bromoindolyl β-D-galactopyranoside (Bluo-gal) and isopropyl β-D-thiogalactopyranoside (IPTG), and then a white single colony isolated on the next day was further cultured to recover Bacmid.

Example 3

Introduction of Bacmid into Insect Cell and Recovery of SFT-1

The above-described Bacmid obtained from a white colony was introduced into an insect cell Sf21 (manufactured by Invitrogen). That is, $9 \times 10^5$ cells/2 ml of the Sf21 cells were added to Sf-900IISFM (manufactured by Invitrogen) containing antibiotics in a 35 mm dish and cultured at 27° C. for 1 hour to adhere the cells. As a solution A, 100 µl of Sf-900IISFM containing no antibiotics was added to 5 µl of Bacmid DNA. As a solution B, 100 µl of Sf-900IISFM containing no antibiotics was added to 6 µl of Cell FECTIN solution (manufactured by Invitrogen). Thereafter, the solution A and solution B were thoroughly mixed and incubated at room temperature for 15 to 45 minutes. After confirming that the cells were adhered, the culture medium was sucked and 2 ml of Sf-900IISFM containing no antibiotics was added. To a solution prepared by mixing the solution A and solution B (lipid-DNA complexes), 800 µl of Sf-900IISFM containing no antibiotics was added and thoroughly mixed. The culture medium was sucked from the cell suspension, and diluted lipid-DNA complexes solution was added to the cells and incubated at 27° C. for 5 hours. Thereafter, the transfection mixture was removed, 2 ml of Sf-900IISFM containing antibiotics was added thereto, and then 72 hours thereafter, the cells were peeled off by pipetting to recover the cells and culture medium. This was centrifuged at 1,200×g for 10 minutes, and the supernatant was stored in another tube (which was used as a first virus solution).

Into a T75 culture flask, $6 \times 10^6$ Sf21 cells/15 ml Sf-900IISFM (manufactured by Invitrogen) (containing antibiotics) was put, 1 ml of the first virus solution was added thereto, followed by culturing at 27° C. for 96 hours. After the culturing, the cells were peeled off by pipetting to recover the cells and culture medium. This was centrifuged at 1,200×g for 10 minutes, and the supernatant was stored in another tube (this was used as a second virus solution).

Furthermore, the $6 \times 10^6$ Sf21 cells/15 ml Sf-900IISFM (manufactured by Invitrogen) (containing antibiotics) was put into a T75 culture flask, and 1 ml of the second virus solution was added thereto, followed by culturing at 27° C. for 72 hours. After the culturing, the cells were peeled off by pipetting to recover the cells and culture medium. The mixture was centrifuged at 1,200×g for 10 minutes, and the supernatant was stored in another tube (which was used as a third virus solution).

In addition, 100 ml of Sf21 cell suspension was put into a 100 ml capacity spinner flask at a density of $6 \times 10^5$ cells/ml, and 1 ml of the third virus solution was added thereto, followed by culturing at 27° C. for about 96 hours. After the culturing, the cells and culture medium were recovered. The mixture was centrifuged at 1,200×g for 10 minutes, and the supernatant was recovered.

Sodium azide, sodium chloride and calcium chloride were added to 10 ml of this culture supernatant to give final concentrations of 0.05% sodium azide, 150 mmol/l sodium chloride and 2 mmol/l calcium chloride. After 50 µl of an anti-Flag antibody gel (Anti-Flag M1 monoclonal antibody Agarose Affinity Gel, manufactured by SIGMA) was added thereto, the mixture was gently stirred for 12 hours. After removing the supernatant by carrying out centrifugation (1,000×g, 3 minutes, 4° C.), washing was carried out three times with Tris buffered saline (TBS) containing 1 mmol/l calcium chloride. By removing excess washing solution by carrying out centrifugation (1,000×g, 3 minutes, 4° C.), an SFT-1-FLAG fusion protein was obtained and used as the enzyme agent of the invention for activity measuring use.

Example 4

Confirmation of SFT-1-FLAG and Measurement of Enzyme Activity (1) Confirmation of SFT-1

Using 5 µl of a gel to which the fusion protein (SFT-1-FLAG) purified above was bound, Western blotting was carried out in accordance with the usual method using a peroxidase-labeled anti-FLAG antibody (Anti-FLAG M2 Peroxidase, manufactured by SIGMA) (FIG. 1). As a result, it was confirmed that the fusion protein of FLAG protein with the novel sulfotransferase expressing in the culture supernatant was recovered and purified.

Figure 2:
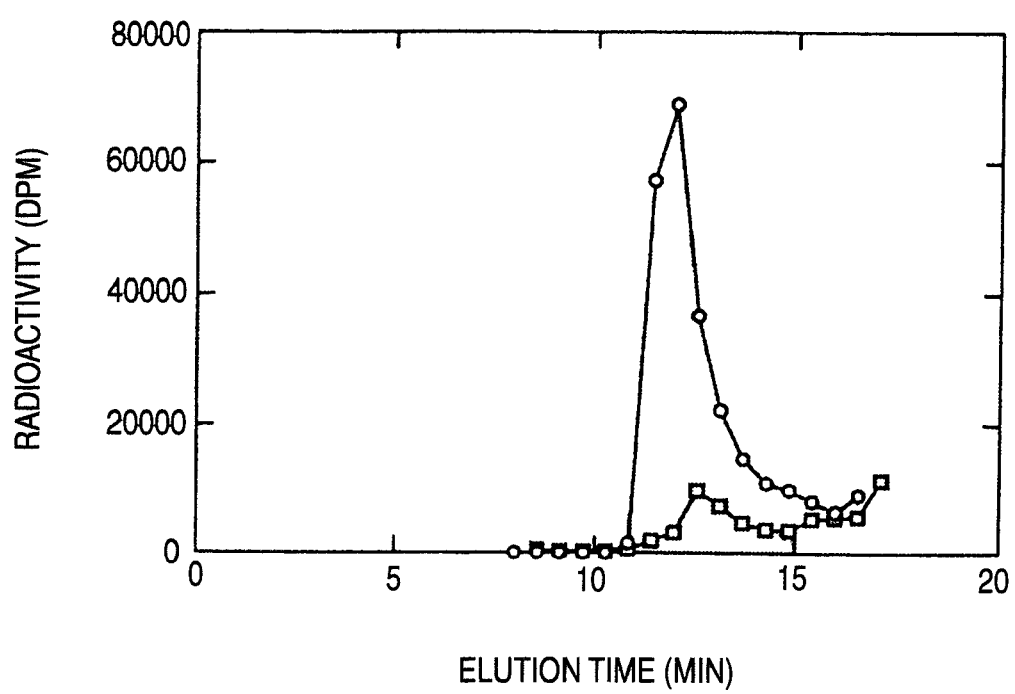
FIG. 2 is a graph showing the activity of transferring a sulfate group to heparan sulfate and heparin. The circles show the sulfate group transferring activity to heparan sulfate, and the squares show the sulfate group transferring activity to heparin.

(2) Measurement of the Activity of the Enzyme Agent of the Invention to Transfer Sulfate Group to Heparan Sulfate and Heparin The fusion protein (SFT-1-FLAG) purified from a culture supernatant was added to 50 mmol/l of an imidazole-hydrochloric acid buffer (pH 6.8) containing 75 µg/ml of protamine hydrochloride, to which were subsequently added [$^{35}$S]-PAPS (5×10$^5$ cpm, manufactured by NEN) as the sulfate donor, and heparan sulfate (derived from bovine kidney: manufactured by Seikagaku Corporation) and heparan (derived from swine intestines: manufactured by SIGMA) (500 µmol/l as the amount of hexosamine) as the sulfate acceptors, and the total volume was adjusted to 50 µl with distilled water. This reaction solution was allowed to react at 37° C. for 20 minutes, and then the reaction was terminated by heating at 100° C. for 3 minutes to deactivate the enzyme. After 130 µl of ethanol containing 1.3% potassium acetate and 0.5 mmol/l EDTA were added thereto, followed by stirring, and then the precipitate obtained by centrifugation was dissolved in 50 µl of distilled water. By again carrying out the ethanol precipitation and dissolution in 50 µl of water, filtration was carried out through a microfilter of 0.22 µm in pore size (manufactured by Millipore), followed by separation by HPLC. The separation was carried out by using G2500PW (manufactured by Tosoh) as the column, and 0.2 mol/l sodium chloride as the mobile phase, at a flow rate of 0.6 ml/min and at a column temperature of 35° C. The eluates from the column were recovered as fractions of every 0.3 ml, and the radioactivity of each fraction was counted by a scintillation counter (FIG. 2). As a result, peak of the radioactivity was detected at a position of the elution time of about 12 minutes. Since this elution time coincides with the elution time of heparan sulfate or heparin as the sulfate acceptor, it was confirmed that it shows the activity of transferring a sulfate group to these two acceptors.

Figure 3:
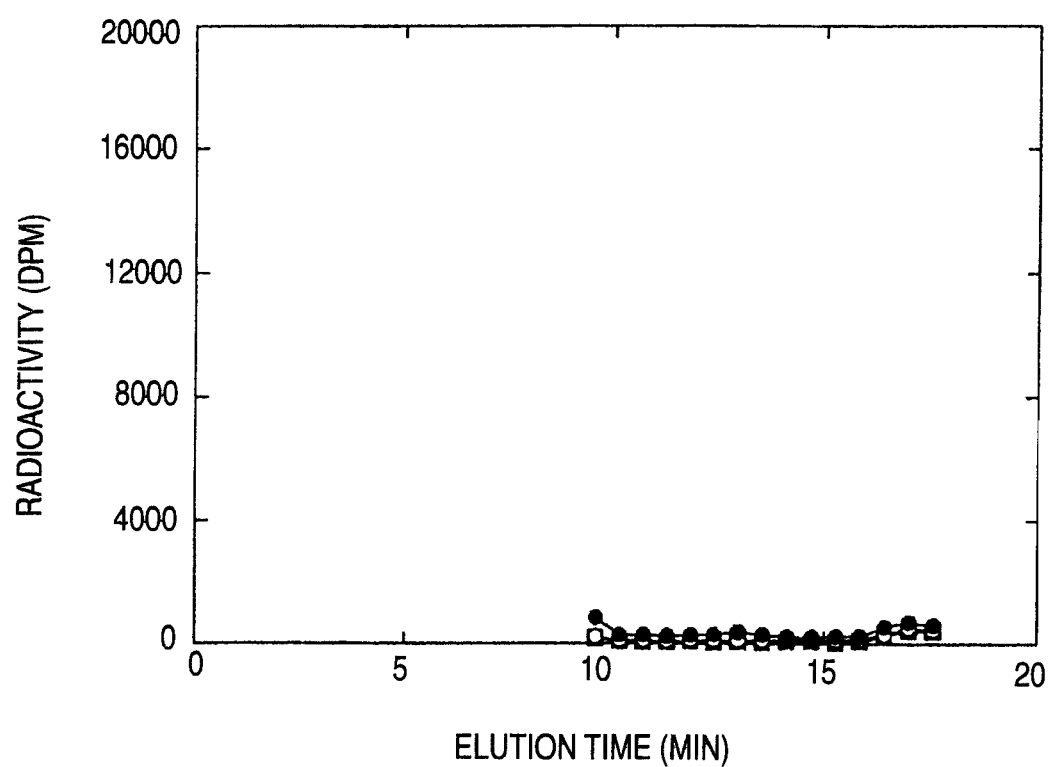
FIG. 3 is a graph showing the activity of transferring a sulfate group to chondroitin sulfate D, chondroitin, dermatan sulfate and dermatan. The open circles, the closed squares, the closed circles and the open squares show the sulfate group transferring activity to chondroitin sulfate D, chondroitin, dermatan sulfate and dermatan, respectively.

In addition, when the sulfate transferring activity was measured under the same conditions of the above-described activity measuring method using chondroitin sulfate D (shark cartilage origin: manufactured by Seikagaku Corporation), chondroitin (prepared by carrying out complete desulfation of bovine bronchus-derived chondroitin sulfate in accordance with the method described in *J. Am. Chem. Soc.*, 79, 152-153 (1957)), dermatan sulfate (swine skin origin: manufactured by Seikagaku Corporation) and desulfated dermatan sulfate (prepared by carrying out complete desulfation of cockscomb-derived dermatan sulfate in accordance with the method described in *J. Am. Chem. Soc.*, 79, 152-153 (1957)) as the sulfate acceptors, the sulfotransferase activity was not observed upon these acceptors (FIG. 3). Accordingly, it was suggested that the SFT-1 has the specific activity for heparan sulfate and heparin.

Example 5

Modification of Heparin by the Inventive Enzyme Agent

Figure 4:
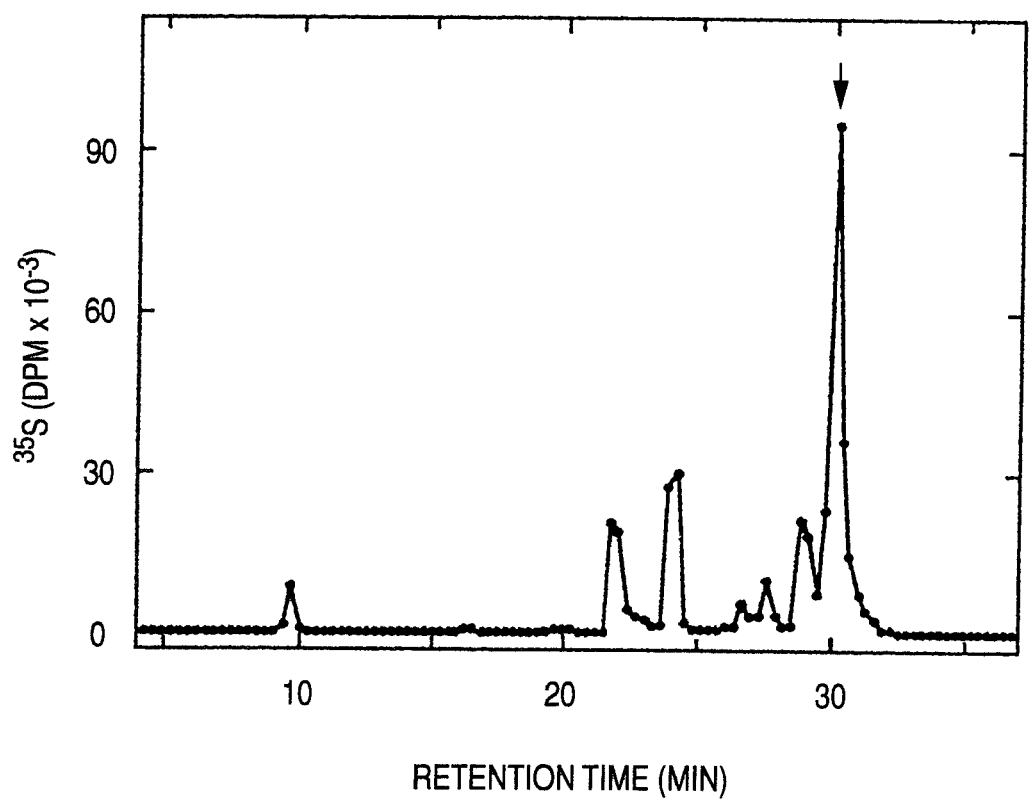
FIG. 4 is a graph showing a radioactivity distribution in each fraction when a glycosaminoglycan prepared by transferring a sulfate group labeled with a radioisotope to heparin by using the enzyme agent of the invention was degraded with heparin lyases, and the thus obtained product was fractionated by high performance liquid chromatography. The ordinate shows radioactivity (dpm×$10^{-3}$) of $^{35}S$, and the abscissa shows retention time (min).

Sulfation reaction of heparin was carried out using the enzyme agent of the invention. The reaction solution contains 11 µg of protamine hydrochloride, 0.3 mg of heparin (manufactured by SIGMA), [$^{35}$S]-PAPS (2.3×10$^7$ dpm: manufactured by Perkin Elmer) and the enzyme agent 1 of the invention (20 µl) in 150 µl of 50 mM imidazole-hydrochloric acid buffer (pH 6.8). After incubation at 37° C. for 3 hours, heparin was recovered by carrying out 70% ethanol precipitation twice. The mixture was allowed to stand at room temperature to evaporate ethanol, dissolved in 30 µl of a buffer for heparin degrading enzyme reaction (20 mM sodium acetate buffer (pH 7.0: contains 2 mM calcium acetate)) and then incubated at 37° C. for 2 hours by adding heparin degrading enzymes (heparinase 150 mU (manufactured by Seikagaku Corporation), heparitinase I 90 mU (manufactured by Seikagaku Corporation) and heparitinase II 60 mU (manufactured by Seikagaku Corporation): these enzymes form an unsaturated disaccharide (ΔHexA1,4GlcN) in which unsaturated uronic acid (ΔHexA) and GlcN are 1,4-glycoside-bound, by hydrolyzing the β 1,4-glucoside binding moiety (GlcNβ1,4HexA) of GlcN and uronic acid (HexA) in the heparin skeleton). Thereafter, the reaction mixture was heated at 100° C. for 1 minute to terminate the reaction, filtered through a microfilter of 0.22 µm in pore size (manufactured by Millipore) and then separated by HPLC. The elution was carried out using CarboPac PA1 (4×250 mm: manufactured by Dionex) and CarboPac PA1 guard column (manufactured by Dionex) as the column and at a flow rate of 0.8 m/min and at a column temperature of 40° C., while effecting 1-6-19-38-70-76-76% of density gradient with 3 mol/l lithium chloride against 0-5-8-15-20-28-40 minutes of elution time. The eluate was fractioned at 0.2 ml, and 10 µl thereof was analyzed by a scintillation counter to confirm eluted position of the radioactivity (FIG. 4). As a result, a peak having strong radioactivity was found at a retention time of 30 minutes.

Figure 5:
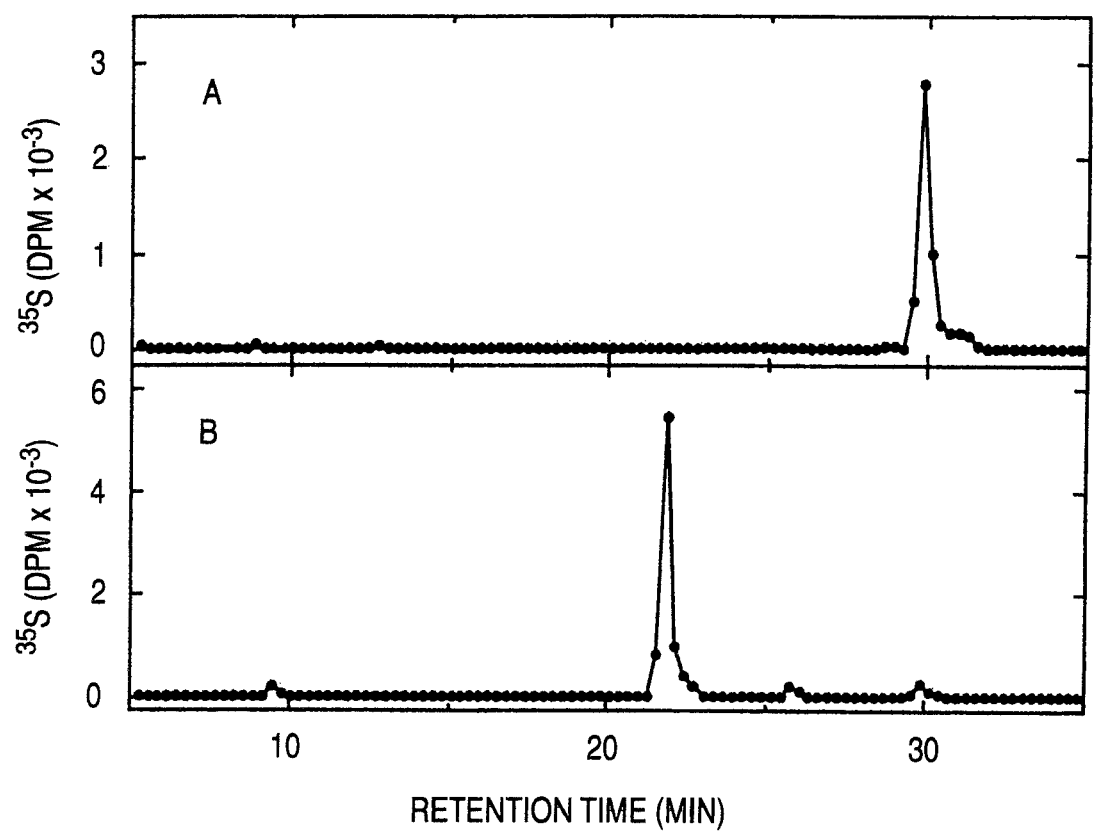
FIG. 5 is a graph showing a radioactivity distribution in each fraction when a "concentrated sample" was digested with heparin 2-sulfatase, and the resulting product was again fractionated by high performance liquid chromatography (B). A indicates a control of not treating with heparin 2-sulfatase. The ordinate shows radioactivity (dpm×$10^{-3}$) of $^{35}S$, and the abscissa shows retention time (min).

Accordingly, the peak appeared at a retention time of 30 minutes was recovered and desalted using Cellulofine G25sf column (1×24 cm: manufactured by Seikagaku Corporation). The thus desalted sample was concentrated to 0.1 ml by a freeze-dryer and used as a "concentrated sample", and 2 µl of the "concentrated sample" was digested with Δ4,5-glucuronate-2-sulfatase (an enzyme which performs desulfation by specifically hydrolyzing the 2-position sulfuric acid ester of unsaturated uronic acid residue: purified in accordance with the method described in *Eur. J. Biochem.*, 145, 607-615 (1984)). As the reaction solution, 5 ml of 20 mmol/l sodium acetate buffer (pH 6.5: contains 0.15% bovine serum albumin and 4.1 mU of heparin 2-sulfatase) was used. After the reaction at 37° C. for 2 hours, the reaction was terminated by heating at 100° C. for 1 minute. After 18 μl of distilled water was added thereto, the mixture was filtered through a filter of 0.22 μm in pore size (manufactured by Millipore) and then separated by HPLC under the same conditions as described above (FIG. 5). As a result, a peak was found at a retention time of about 30.5 minutes in the control which was not digested with heparin 2-sulfatase (FIG. 5A), but retention time of the peak was shifted to about 22 minutes in the concentrated sample treated with Δ4,5-glucuronate-2-sulfatase (FIG. 5B). That is, since shifting of the peak was observed by the treatment with the enzyme which specifically performs desulfation of the 2-position sulfate group of unsaturated uronic acid, it was confirmed that the unsaturated disaccharide contained in the concentrated sample contains a ΔHexA(2S) structure of the following formula (5).

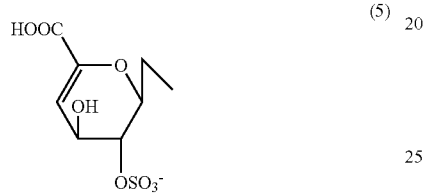

(5)

Next, 2 μl of the above-described "concentrated sample" was mixed with 2 μl of 70 mM mercury acetate (pH 5.0) and allowed to stand at room temperature for 10 minutes to remove the unsaturated uronic acid (the unsaturated uronic acid alone in the unsaturated disaccharide is specifically degraded by this reaction: *Biochem. J.* 245, 795-804 (1987)), further mixed with 2 μl of 1 mol/l sodium carbonate buffer (pH 9.0) and 2 μl of 0.5 mol/l sodium tetrahydroborate (0.1 mol/l sodium hydroxide solution) and incubated at 50° C. for 30 minutes to carry out reduction reaction, and then separated by HPLC under the same conditions as described above (FIG. 6). When the elution pattern of the "concentrated sample" after degradation of the unsaturated uronic acid (FIG. 6A) was compared with the elution pattern of the standard sample labeled by the reduction reaction with sodium [³H]tetrahydroborate (GlcN(NS,3S): peak 1 around 14 minutes: (GlcN(NS,3S,6S): peak 2 around 22 to 23 minutes) (FIG. 6B), retention time of the sample coincided with that of (GlcN(NS,3S,6S) (peak 2). Based on this, it was found that the "concentrated sample" after degradation of the unsaturated uronic acid is GlcN in which the 2-position amino group, the 3-position hydroxyl group and the 6-position hydroxyl group are sulfated.

Figure 6:
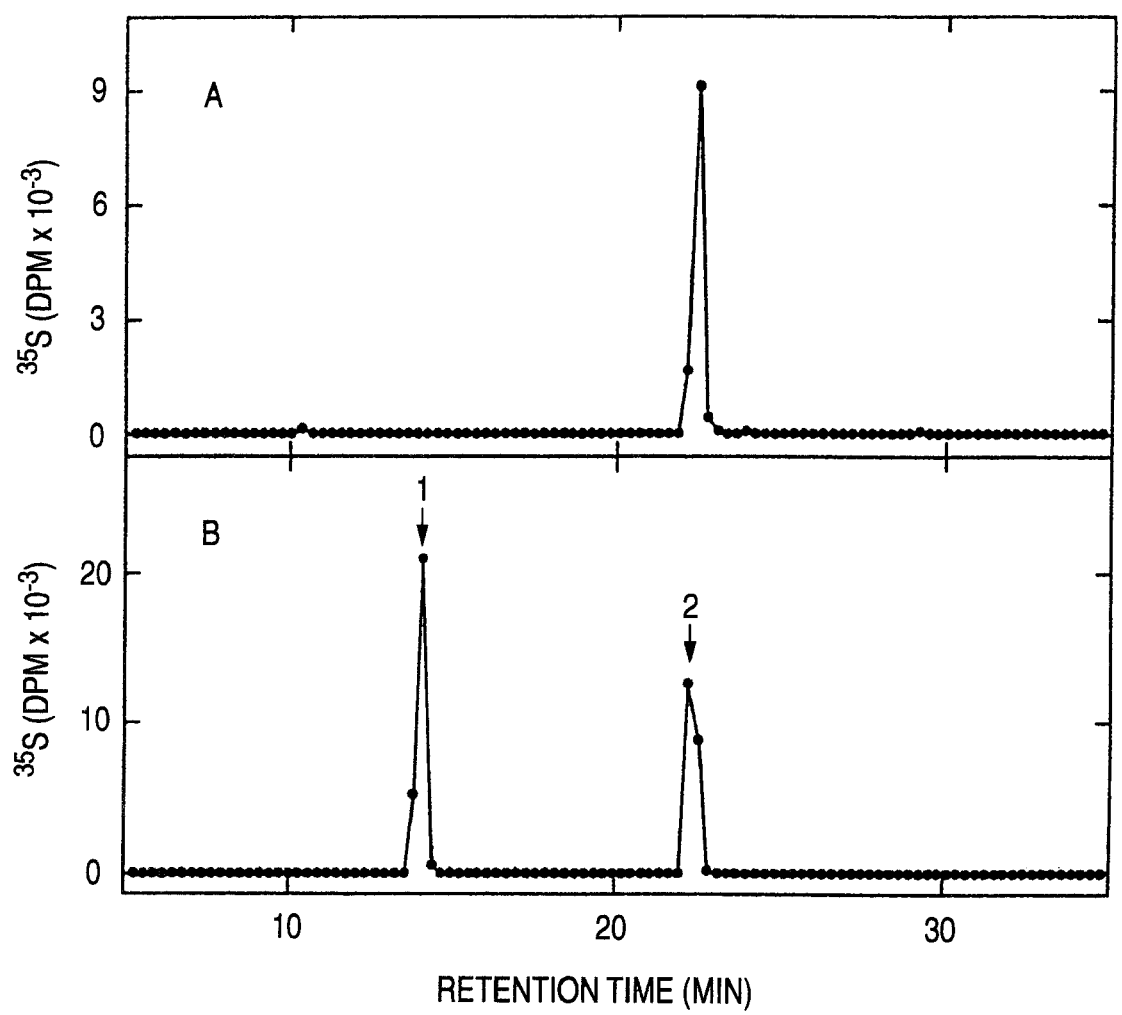
FIG. 6 is a graph showing a radioactivity distribution in each fraction when a sample obtained by specifically degrading only the unsaturated uronic acid of the "concentrated sample" was fractionated by high performance liquid chromatography (A). B is a graph showing a radioactivity distribution in each fraction when a standard sample labeled with a radioisotope was fractionated by high performance liquid chromatography in the same manner. The ordinate shows radioactivity (dpm×$10^{-3}$) of $^{35}S$ or $^{3}H$, and the abscissa shows retention time (min).

From the results of FIG. 5 and FIG. 6, it was confirmed that the unsaturated disaccharide contained in the concentrated sample is an unsaturated disaccharide (ΔHexA(2S)-GlcN(NS,3S,6S)) shown by the following formula (6), and it was shown that the structure represented by the above-described formula (1) is contained in the glycosaminoglycan before degradation with heparin degrading enzymes.

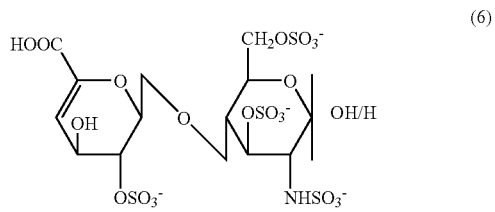

(6)

Figure 7:
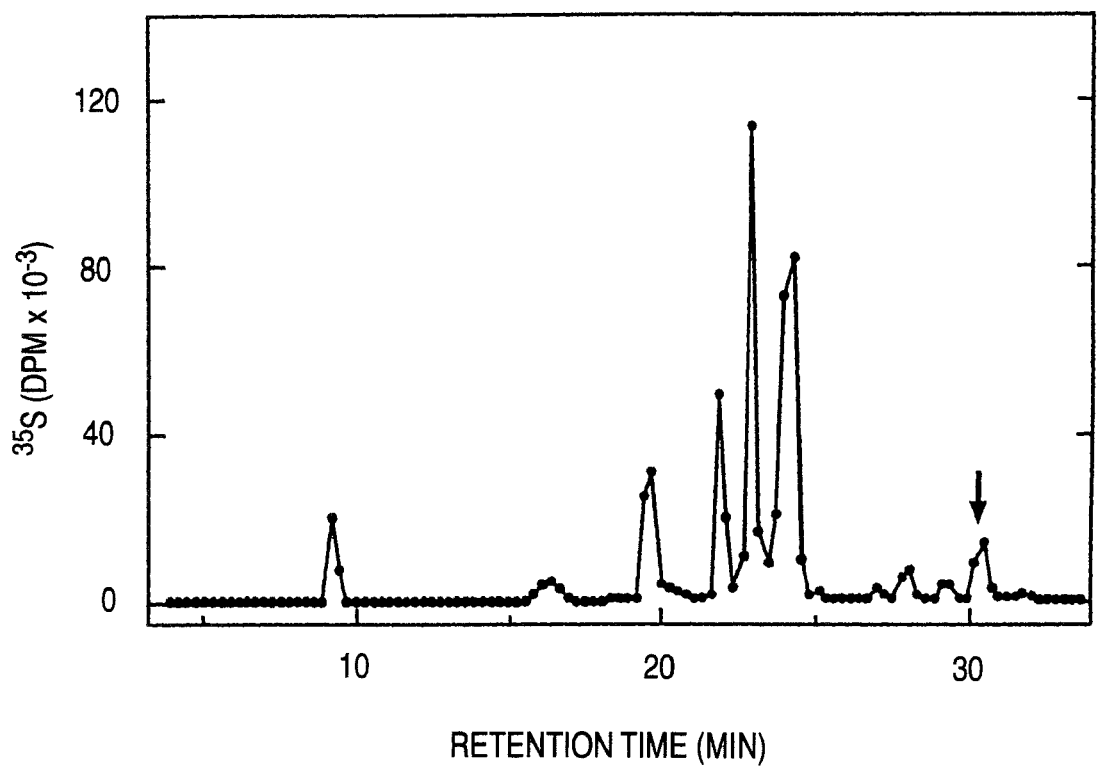
FIG. 7 is a graph showing a radioactivity distribution in each fraction when the unsaturated disaccharide obtained by degrading heparan sulfate to which the "sulfate group labeled with a radioisotope" had been transferred using the enzyme agent 1 of the invention was fractionated by high performance liquid chromatography. The ordinate shows radioactivity (dpm×10$^{-3}$) of $^{35}$S, and the abscissa shows retention time (min).

When heparan sulfate (manufactured by SIGMA) was sulfated using the enzyme agent of the invention under the same sulfation reaction conditions as described above and digested with heparin degrading enzymes in the same manner as described above, and the thus obtained sample was separated by HPLC, a peak was detected at a retention time of about 30.5 minutes (the peak shown by an arrow in FIG. 7), though the formed amount was smaller than the case of heparin. Since this is the same retention time of ΔHexA(2S)-GlcN(NS,3S,6S) confirmed by heparin, it was found that the glycosaminoglycan containing the structure represented by the above-described formula (1) was also formed when heparan sulfate was used as the sulfate group acceptor.

INDUSTRIAL APPLICABILITY

A nucleic acid comprising a nucleotide sequence encoding a polypeptide of a novel heparan sulfate sulfotransferase capable of selectively transferring sulfate group to heparan sulfate is obtained by the invention. Furthermore, a polypeptide expressed by the nucleic acid is obtained.

Also, since a nucleic acid comprising a nucleotide sequence encoding a polypeptide of a novel heparan sulfate sulfotransferase was obtained by the invention, it is expected that the enzyme can be mass-produced to an industrially applicable level. Furthermore, a glycosaminoglycan having a new structure is provided based on the enzyme activity possessed by the enzyme.

The invention claimed is:

1. An isolated nucleic acid selected from the group consisting of (I), (II) and (III):
   (I) a cDNA encoding a polypeptide consisting of amino acids 37 to 346 of SEQ ID NO:2, or encoding a polypeptide consisting of an amino acid sequence at least 95% identical to the amino acid sequence of SEQ ID NO:2 and having an activity of transferring a sulfate group to a glycosaminoglycan which is a sulfate group acceptor;
   (II) a cDNA consisting of the nucleotide sequence of SEQ ID NO:1; and
   (III) an isolated DNA which hybridizes under stringent conditions to the cDNA according to (I) or (II) and which encodes a polypeptide having an activity of transferring a sulfate group to a glycosaminoglycan which is a sulfate group acceptor, or an isolated DNA fully complementary to the cDNA according to (I) or (II)
   wherein hybridization under the stringent conditions occurs at 42° C. in the presence of 50% formamide, 5×Denhardt's solution, 0.5% SDS (sodium dodecyl sulfate), 5×SSPE (sodium chloride/sodium phosphate/ethylenediaminetetraacetic acid) buffer and 100 µg/ml denatured salmon sperm DNA.

2. An expression vector which comprises the nucleic acid according to claim 1.

3. An isolated host cell which comprises the expression vector according to claim 2.

4. A process for producing a polypeptide or a sulfotransferase, which comprises:
   growing the host cell according to claim 3, and recovering a polypeptide encoded by the expression vector of said host cell.

5. An expression vector which comprises a nucleic acid selected from the group consisting of (I), (II) and (III):
   (I) a nucleic acid consisting of a polynucleotide sequence encoding a polypeptide consisting of amino acids 37 to 346 of SEQ ID NO:2, or encoding a polypeptide consisting of an amino acid sequence at least 95% identical to the amino acid sequence of SEQ ID NO:2 and having an activity of transferring a sulfate group to a glycosaminoglycan which is a sulfate group acceptor;
   (II) a nucleic acid consisting of the nucleotide sequence of SEQ ID NO:1; and
   (III) a nucleic acid which hybridizes under stringent conditions to the nucleic acid according to (I) or (II) and which encodes a polypeptide having an activity of transferring a sulfate group to a glycosaminoglycan which is a sulfate group acceptor, or a nucleic acid fully complementary to the nucleotide sequence of the nucleic acid according to (I) or (II)
   wherein hybridization under the stringent conditions occurs at 42° C. in the presence of 50% formamide, 5×Denhardt's solution, 0.5% SDS (sodium dodecyl sulfate), 5×SSPE (sodium chloride/sodium phosphate/ethylenediaminetetraacetic acid) buffer and 100 µg/ml denatured salmon sperm DNA.

6. An isolated host cell which comprises the expression vector according to claim 5.

7. A process for producing a polypeptide or a sulfotransferase, which comprises:
   growing the host cell according to claim 6, and recovering a polypeptide encoded by the expression vector of said host cell.

* * * * *

SEQUENCE LISTING

<160> NUMBER OF SEQ ID NOS: 16

<210> SEQ ID NO 1
<211> LENGTH: 1041
<212> TYPE: DNA
<213> ORGANISM: Homo sapiens
<220> FEATURE:
<221> NAME/KEY: CDS
<222> LOCATION: (1)..(1041)

<400> SEQUENCE: 1

```
atg cta ttc aaa cag cag gcg tgg ctg aga cag aag ctc ctg gtg ctg      48
Met Leu Phe Lys Gln Gln Ala Trp Leu Arg Gln Lys Leu Leu Val Leu
 1               5                  10                  15 gga agc ctt gcc gtt ggg agt ctc ctg tat cta gtc gcc aga gtt ggg      96
```

```
                Gly Ser Leu Ala Val Gly Ser Leu Leu Tyr Leu Val Ala Arg Val Gly
                             20                  25                  30 agc ttg gat agg cta caa ccc att tgc ccc att gaa ggt cga ctg ggt        144
Ser Leu Asp Arg Leu Gln Pro Ile Cys Pro Ile Glu Gly Arg Leu Gly
             35                  40                  45 gga gcc cgc act cag gct gaa ttc cca ctt cgc gcc ctg cag ttt aag        192
Gly Ala Arg Thr Gln Ala Glu Phe Pro Leu Arg Ala Leu Gln Phe Lys
 50                  55                  60 cgt ggc ctg ctg cac gag ttc cgg aag ggc aac gct tcc aag gag cag        240
Arg Gly Leu Leu His Glu Phe Arg Lys Gly Asn Ala Ser Lys Glu Gln
 65                  70                  75                  80 gtt cgc ctc cat gac ctg gtc cag cag ctc ccc aag gcc att atc att        288
Val Arg Leu His Asp Leu Val Gln Gln Leu Pro Lys Ala Ile Ile Ile
                 85                  90                  95 ggg gtg agg aaa gga ggc aca agg gcc ctg ctt gaa atg ctg aac cta        336
Gly Val Arg Lys Gly Gly Thr Arg Ala Leu Leu Glu Met Leu Asn Leu
            100                 105                 110 cat ccg gca gta gtc aaa gcc tct caa gaa atc cac ttt ttt gat aat        384
His Pro Ala Val Val Lys Ala Ser Gln Glu Ile His Phe Phe Asp Asn
        115                 120                 125 gat gag aat tat ggt aag ggc att gag tgg tat agg aaa aag atg cct        432
Asp Glu Asn Tyr Gly Lys Gly Ile Glu Trp Tyr Arg Lys Lys Met Pro
130                 135                 140 ttt tcc tac cct cag caa atc aca att gaa aag agc cca gca tat ttc        480
Phe Ser Tyr Pro Gln Gln Ile Thr Ile Glu Lys Ser Pro Ala Tyr Phe
145                 150                 155                 160 atc aca gag gag gtt cca gaa agg att tac aaa atg aac tca tcc atc        528
Ile Thr Glu Glu Val Pro Glu Arg Ile Tyr Lys Met Asn Ser Ser Ile
                165                 170                 175 aag ttg ttg atc att gtc agg gag cca acc aca aga gct att tct gat        576
Lys Leu Leu Ile Ile Val Arg Glu Pro Thr Thr Arg Ala Ile Ser Asp
            180                 185                 190 tat act cag gtg cta gag ggg aag gag agg aag aac aaa act tat tac        624
Tyr Thr Gln Val Leu Glu Gly Lys Glu Arg Lys Asn Lys Thr Tyr Tyr
        195                 200                 205 aag ttt gag aag ctg gcc ata gac cct aat aca tgc gaa gtg aac aca        672
Lys Phe Glu Lys Leu Ala Ile Asp Pro Asn Thr Cys Glu Val Asn Thr
210                 215                 220 aaa tac aaa gca gta aga acc agc atc tac acc aaa cat ctg gaa agg        720
Lys Tyr Lys Ala Val Arg Thr Ser Ile Tyr Thr Lys His Leu Glu Arg
225                 230                 235                 240 tgg ttg aaa tac ttt cca att gag caa ttt cat gtc gtc gat gga gat        768
Trp Leu Lys Tyr Phe Pro Ile Glu Gln Phe His Val Val Asp Gly Asp
                245                 250                 255 cgc ctc atc acg gaa cct ctg cca gaa ctt cag ctc gtg gag aag ttc        816
Arg Leu Ile Thr Glu Pro Leu Pro Glu Leu Gln Leu Val Glu Lys Phe
            260                 265                 270 cta aat ctg cct cca agg ata agt caa tac aat tta tac ttc aat gct        864
Leu Asn Leu Pro Pro Arg Ile Ser Gln Tyr Asn Leu Tyr Phe Asn Ala
        275                 280                 285 acc aga ggg ttt tac tgc ttg cgg ttt aat att atc ttt aat aag tgc        912
Thr Arg Gly Phe Tyr Cys Leu Arg Phe Asn Ile Ile Phe Asn Lys Cys
290                 295                 300 ctg gcg ggc agc aag ggg cgc att cat cca gag gtg gac ccc tct gtc        960
Leu Ala Gly Ser Lys Gly Arg Ile His Pro Glu Val Asp Pro Ser Val
305                 310                 315                 320 att act aaa ttg cgc aaa ttc ttt cat cct ttt aat caa aaa ttt tac       1008
Ile Thr Lys Leu Arg Lys Phe Phe His Pro Phe Asn Gln Lys Phe Tyr
                325                 330                 335 cag atc act ggg agg aca ttg aac tgg ccc taa                           1041
```

```
Gln Ile Thr Gly Arg Thr Leu Asn Trp Pro
            340                 345

<210> SEQ ID NO 2
<211> LENGTH: 346
<212> TYPE: PRT
<213> ORGANISM: Homo sapiens

<400> SEQUENCE: 2

Met Leu Phe Lys Gln Gln Ala Trp Leu Arg Gln Lys Leu Leu Val Leu
  1               5                  10                  15

Gly Ser Leu Ala Val Gly Ser Leu Leu Tyr Leu Val Ala Arg Val Gly
             20                  25                  30

Ser Leu Asp Arg Leu Gln Pro Ile Cys Pro Ile Glu Gly Arg Leu Gly
         35                  40                  45

Gly Ala Arg Thr Gln Ala Glu Phe Pro Leu Arg Ala Leu Gln Phe Lys
     50                  55                  60

Arg Gly Leu Leu His Glu Phe Arg Lys Gly Asn Ala Ser Lys Glu Gln
 65                  70                  75                  80

Val Arg Leu His Asp Leu Val Gln Gln Leu Pro Lys Ala Ile Ile Ile
                 85                  90                  95

Gly Val Arg Lys Gly Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Gly Lys Gly Ile Glu Trp Tyr Arg Lys Lys Met Pro
    130                 135                 140

Phe Ser Tyr Pro Gln Gln Ile Thr Ile Glu Lys Ser Pro Ala Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Asp
            180                 185                 190

Tyr Thr Gln Val Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220

Lys Tyr Lys Ala Val Arg Thr Ser Ile Tyr Thr Lys His Leu Glu Arg
225                 230                 235                 240

Trp Leu Leu Tyr Phe Pro Ile Glu Gln Phe His Val Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Ile Phe Asn Lys Cys
    290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr
                325                 330                 335

Gln Ile Thr Gly Arg Thr Leu Asn Trp Pro
            340                 345

<210> SEQ ID NO 3
<211> LENGTH: 12
```

```
<212> TYPE: DNA
<213> ORGANISM: Artificial Sequence
<220> FEATURE:
<223> OTHER INFORMATION: Description of Artificial Sequence: 5' Primer
      for PCR

<400> SEQUENCE: 3
ctacaaccca tt                                                           12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: 3' Primer
      for PCR

<400> SEQUENCE: 4
ttagggccag tt                                                           12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: 5' Primer
      for PCR

<400> SEQUENCE: 5
atgctattca aa                                                           12

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: 5' Primer
      for PCR (GP-226)

<400> SEQUENCE: 6
cggaactcgt gcagcaggcc acgc                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: 5' primer
      for PCR (GP-224)

<400> SEQUENCE: 7
tcgaccttca atggggcaaa tggg                                              24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: 5' primer
      for PCR (SFTex2F)

<400> SEQUENCE: 8
actggggaac cagaaaaatg aaaag                                             25

<210> SEQ ID NO 9
<211> LENGTH: 25
<212> TYPE: DNA
<213> ORGANISM: Artificial Sequence
```

```
<220> FEATURE:
<223> OTHER INFORMATION: Description of Artificial Sequence: 3' primer
      for PCR (SFTex2R)

<400> SEQUENCE: 9
gtgtctccag gcacaacaca tagtg                                             25

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: 5' primer
      for PCR (SFTgateF2)

<400> SEQUENCE: 10
ggggacaagt ttgtacaaaa aagcaggctt ctttaagcgt ggcctgctgc acgag            55

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: 3' primer
      for PCR (SFTgateTstop)

<400> SEQUENCE: 11
ggggaccact ttgtacaaga aagctgggtt tagggccagt tcaatgtcct ccc              53

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Ig kappa
      signal sequence

<400> SEQUENCE: 12

Met His Phe Gln Val Gln Ile Phe Ser Phe Leu Leu Ile Ser Ala Ser
 1               5                  10                  15

Val Ile Met Ser Arg Gly
             20

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 13

Asp Tyr Lys Asp Asp Asp Lys
 1               5

<210> SEQ ID NO 14
<211> LENGTH: 94
<212> TYPE: DNA
<213> ORGANISM: Artificial Sequence
<220> FEATURE:
<223> OTHER INFORMATION: Description of Artificial Sequence: OT3 seuqnce

<400> SEQUENCE: 14
gatcatgcat tttcaagtgc agattttcag cttcctgcta atcagtgcct cagtcataat       60
gtcacgtgga gattacaagg acgacgatga caag                                   94
```

```
<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: OT20
      sequence

<400> SEQUENCE: 15
cgggatccat gcattttcaa gtgcag                                          26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: OT21
      sequence

<400> SEQUENCE: 16
ggaattcttg tcatcgtcgt ccttg                                           25
```